United States Patent
Roland

(10) Patent No.: US 11,452,461 B2
(45) Date of Patent: Sep. 27, 2022

(54) METHOD FOR POSITIONING A PATIENT WITHIN A PATIENT RECEIVING AREA FOR A MAGNETIC RESONANCE EXAMINATION AND A CORRESPONDING MAGNETIC RESONANCE SYSTEM

(71) Applicant: Siemens Healthcare GmbH, Erlangen (DE)

(72) Inventor: Joerg Roland, Hemhofen (DE)

(73) Assignee: Siemens Healthcare GmbH, Erlangen (DE)

( * ) Notice: Subject to any disclaimer, the term of this patent is extended or adjusted under 35 U.S.C. 154(b) by 524 days.

(21) Appl. No.: 16/542,610

(22) Filed: Aug. 16, 2019

(65) Prior Publication Data
US 2020/0054240 A1 Feb. 20, 2020

(30) Foreign Application Priority Data
Aug. 16, 2018 (DE) ...................... 10 2018 213 781.1

(51) Int. Cl.
*A61B 5/055* (2006.01)
*G01R 33/54* (2006.01)
*G01R 33/30* (2006.01)

(52) U.S. Cl.
CPC ............ *A61B 5/055* (2013.01); *G01R 33/307* (2013.01); *G01R 33/543* (2013.01)

(58) Field of Classification Search
CPC ..... A61B 5/055; G01R 33/307; G01R 33/543
See application file for complete search history.

(56) References Cited

U.S. PATENT DOCUMENTS

| | | | |
|---|---|---|---|
| 5,666,056 A | 9/1997 | Cuppen | |
| 6,822,447 B1 * | 11/2004 | Yamagata | G01R 33/3806 324/309 |
| 2004/0186374 A1 | 9/2004 | Satragno et al. | |
| 2015/0201863 A1 | 7/2015 | Flammang et al. | |

FOREIGN PATENT DOCUMENTS

| | | | |
|---|---|---|---|
| DE | 102014201242 A1 | 7/2015 | |
| EP | 1460443 A2 | 9/2004 | |
| JP | H09299352 A * | 11/1997 | ............... A61B 5/05 |

OTHER PUBLICATIONS

German action dated Jul. 8, 2019, for Application No. 10 2018 213 781.1.

* cited by examiner

*Primary Examiner* — G. M. A Hyder
(74) *Attorney, Agent, or Firm* — Banner & Witcoff Ltd.

(57) ABSTRACT

Techniques are disclosed for positioning a patient within a patient receiving area for a magnetic resonance examination. The techniques may include positioning the patient on a mobile patient table of a patient support facility and moving the patient table in a first horizontal direction until a region of the patient to be examined is arranged in a field of view of a patient receiving area of a magnetic resonance system. Moreover, the patient positioning techniques may include moving the patient table in a second horizontal direction and/or in a vertical direction within the patient receiving area, and acquiring medical magnetic resonance data of the region of the patient to be examined.

14 Claims, 2 Drawing Sheets

METHOD FOR POSITIONING A PATIENT WITHIN A PATIENT RECEIVING AREA FOR A MAGNETIC RESONANCE EXAMINATION AND A CORRESPONDING MAGNETIC RESONANCE SYSTEM

CROSS-REFERENCE TO RELATED APPLICATIONS

The present application claims the benefit of the filing date of German patent application no. DE 10 2018 213 781.1, filed on Aug. 16, 2018, the contents of which are incorporated herein by reference in their entirety.

TECHNICAL FIELD

The present disclosure relates to a method for positioning a patient within a patient receiving area for a magnetic resonance examination and also to a corresponding magnetic resonance system for carrying out the method. Furthermore, the present disclosure relates to a computer program product with a program, which is designed for carrying out the method for positioning a patient within a patient receiving area for a magnetic resonance examination and also to an electronically readable data medium with the computer program product.

BACKGROUND

During a diagnostic and/or clinical evaluation of magnetic resonance image data, image artifacts represent an issue, since image artifacts can lead to a misinterpretation of the image data and thus to misdiagnoses. Causes of such image artifacts can be imaging materials for example, with the imaging materials being arranged and/or positioned within a spatially localized and/or restricted area of a patient receiving area of the magnetic resonance system. Such imaging materials can comprise organs and/or further parts of the patient's body, for example, which are arranged next to the region of the patient's body to be examined.

SUMMARY

The underlying object of the present disclosure is to provide a method for reducing and/or eliminating disruptive effects, such as artifacts, from the diagnostic imaging data. The object is achieved by the features of the independent claims. Advantageous embodiments are further described in the dependent claims and throughout the disclosure.

The disclosure is based on a method for positioning a patient within a patient receiving area for a magnetic resonance examination with the following steps:

Positioning the patient on a movable patient table of a patient support;

Moving the patient table in a first horizontal direction until a region of the patient to be examined is arranged in a field of view of a patient receiving area of a magnetic resonance system;

Moving the patient table in a second horizontal direction and/or in a vertical direction within the patient receiving area; and Acquiring medical magnetic resonance data of the region of the patient to be examined.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

Figure 1:
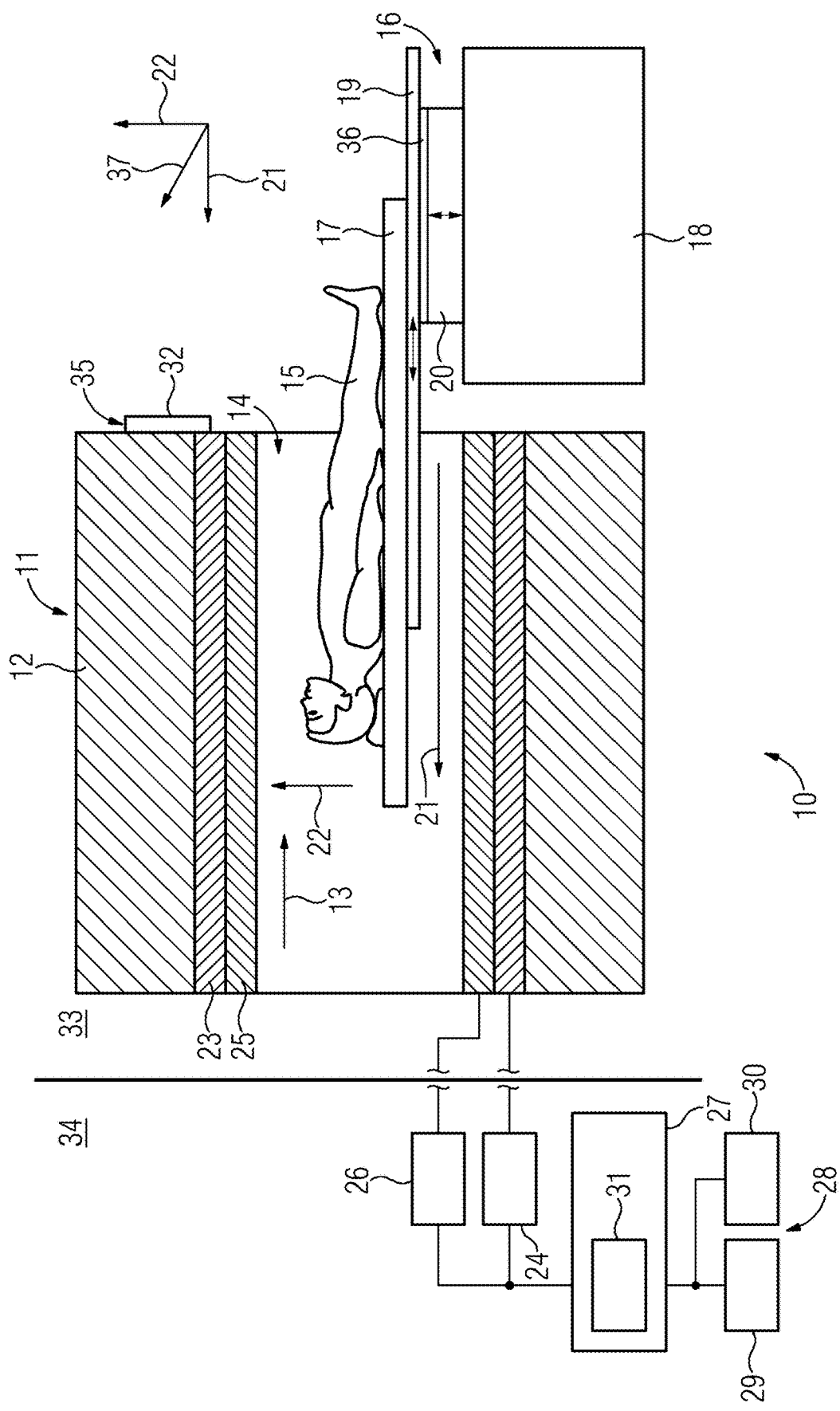
Figure 2:
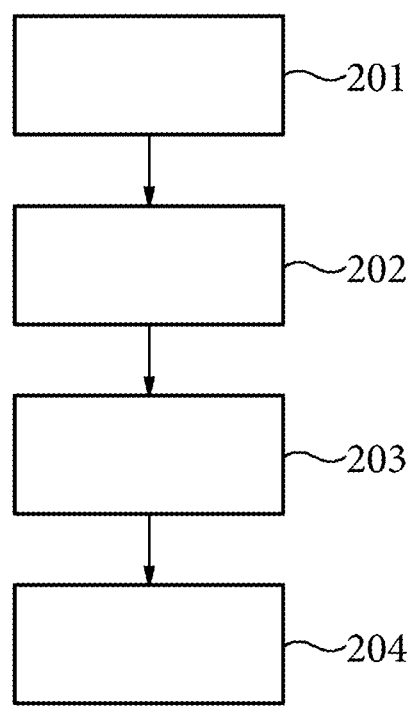

FIG. 1 shows an example magnetic resonance system as a schematic diagram, in accordance with an embodiment of the present disclosure; and FIG. 2 shows a flow diagram of an example method for positioning a patient within a patient receiving area for a magnetic resonance examination, in accordance with an embodiment of the present disclosure.

The exemplary embodiments of the present disclosure will be described with reference to the accompanying drawings. The drawing in which an element first appears is typically indicated by the leftmost digit(s) in the corresponding reference number.

DETAILED DESCRIPTION

As further discussed herein, the magnetic resonance examination of patients is undertaken by means of a medical magnetic resonance system. Such magnetic resonance facilities have a scanner unit, which is arranged within an examination room, and a control unit with a user interface, which is arranged within a control room. The examination room is embodied separately from the control room and is decoupled from the control room with respect to an exchange of electromagnetic radiation. The scanner unit comprises a main magnet, a gradient coil unit, and a radio-frequency antenna unit. The scanner unit also comprises a centrally arranged, tunnel-shaped and/or cylindrical opening, which comprises the patient receiving area. The patient receiving area in this case extends in a first horizontal direction through the scanner unit. The patient receiving area can also be open to the side in some embodiments. The patient receiving area is configured to receive the patient, and in particular to receive the region of the patient to be examined during the magnetic resonance examination. Located within the patient receiving area is a field of view (FoV) of the magnetic resonance system, within which an object to be examined (e.g., a region of the patient to be examined) is to be positioned for a magnetic resonance examination. The FoV of a magnetic resonance system may include a detection area of the magnetic resonance system, within which magnetic resonance signals are acquired.

The magnetic resonance system may further include a patient support configured to position the patient within the patient receiving area. The patient support may comprise a movable patient table. Typically, such a patient table has a first horizontal adjustment unit, by means of which the patient can be moved in a first horizontal direction into the patient receiving area. The first horizontal direction may comprise a direction of a longitudinal extent of the patient table and/or a direction of a longitudinal extent of the patient receiving area. Moreover, the patient support (e.g. the mobile patient table), can also have a second horizontal adjustment unit, by means of which the patient table is moved and/or displaced in a second horizontal direction. The horizontal adjustment unit may be configured in such a way that the patient table is also configured to be movable and/or displaced within the patient receiving area of the scanner unit in the second horizontal direction. A second horizontal direction is to be understood as a direction that is essentially aligned at right angles to the first horizontal direction, and which further comprises a direction of a width of the patient table.

The first horizontal direction, together with the second horizontal direction, spans a plane that is at right angles to a weight force acting on the patient support. Moreover, the patient support (e.g. the movable patient table), can also have a vertical adjustment unit, by means of which the patient table is moved and/or displaced in a vertical direction. The vertical adjustment unit may be configured in such a way that the patient table is also movable and/or displaced in a vertical direction within the patient receiving area of the scanner unit. A vertical direction is to be understood as a direction that is essentially parallel to a weight force acting on the patient table or which is essentially antiparallel and/or in opposition to a weight force acting on the patient table. Moving the patient table in a vertical direction can also comprise tilting the patient table, such that the patient table is tilted about a tilt axis that is aligned, for instance, in parallel to the second horizontal direction.

For the magnetic resonance examination, the patient is initially positioned on the patient table depending on the region of the patient to be examined. For an impending head examination, for example, the patient is positioned on the patient table in such a way that the patient can be moved head first into the patient receiving area. As another example, for an impending knee examination, the patient is positioned on the patient table in such a way that the patient can be moved feet first into the patient receiving area.

The embodiments described herein advantageously enable disruptive effects in the image data, such as image artifacts for example, to be reduced and/or prevented. This may be the result of, for example, the movement and/or a positioning of the patient table in the second horizontal direction and/or in the vertical direction, imaging regions, and/or materials. The materials may not be included in the region of the patient to be examined, and instead can be positioned outside a critical field extent and/or outside a critical field area of the magnetic field of the magnetic resonance system for the acquisition of medical magnetic resonance data. A field extent of the magnetic field within the patient receiving area is described by an overlaying of a basic magnetic field with a gradient field. A field strength of the magnetic field falls away at edge areas of the patient receiving area and leads to a critical field extent of the magnetic field. Objects and/or imaging materials that are arranged within the critical field extent can lead to undesired faults, such as undesired artifacts, in the acquisition of magnetic resonance data.

As an example, for a magnetic resonance examination of the patient's liver, the patient table can be displaced far enough in the vertical direction (e.g. upwards), such that the arms of the patient are arranged outside the critical field extent and also outside the detection area of the magnetic resonance system. If the patient's arms were arranged within the critical field extent and/or within the detection area of the magnetic resonance system, this could lead to streaking artifacts in the liver image data.

Moreover, as a result of the positioning of the patient in the second horizontal direction and/or in the vertical direction within the patient receiving area, an advantageous positioning of the region of the patient to be examined within the isocenter of the magnetic resonance system is achieved, and thus an optimal condition is provided for a high image quality of the acquired magnetic resonance image data. The isocenter of a magnetic resonance system may comprise an area that has the most ideal conditions, such as a homogeneous magnetic field for instance, for a magnetic resonance examination.

As an example, the method embodiments described herein can be advantageously applied in a magnetic resonance system, with a diameter of the patient receiving area of at least 50 cm, since a positioning play in the second horizontal direction and/or in the vertical direction is available for the positioning of the patient within the patient receiving area. As another example, the method embodiments described herein can be applied in a magnetic resonance system with a diameter of the patient receiving area of at least 60 cm, since a positioning play in the second horizontal direction and/or in the vertical direction is available for the positioning of the patient within the patient receiving area. As an additional example, the method embodiments described herein can be applied in a magnetic resonance system with a diameter of the patient receiving area of at least 70 cm, since a positioning play in the second horizontal direction and/or in the vertical direction is available for the positioning of the patient within the patient receiving area. As yet another example, the method embodiments described herein can be applied in a magnetic resonance system with a diameter of the patient receiving area of at least 80 cm, since a positioning play in the second horizontal direction and/or in the vertical direction is available for the positioning of the patient within the patient receiving area.

In an advantageous development of the disclosure, there can be a provision for the processing unit to determine a position of the patient table in the second horizontal direction and/or in the vertical direction as a function of a planned magnetic resonance examination that indicates a desired position of the patient and/or region to be scanned. This enables a simple and optimal positioning of the patient within the patient receiving area to be achieved, thus yielding a high image quality of the subsequent image data in the subsequent magnetic resonance examination.

If information about the planned and/or impending magnetic resonance examination is already available, embodiments include the region of the patient to be examined for the planned and/or impending magnetic resonance examination being also substantially defined. For example, the processing unit as further describe herein can define a position of the patient and/or of the patient table in such a way that the region of the patient to be examined is positioned within the isocenter, and any regions that might disturb the impending magnetic resonance examination are arranged outside the critical field extent. Continuing this example, the processing unit can also take into account a dimension of the patient receiving area in determining the position of the patient table in the second horizontal direction and/or in the vertical direction, so that too small a distance between the patient and a housing surrounding the patient receiving area can be prevented.

In an advantageous development of the disclosure, there can be a provision for the processing unit to determine a position of the patient table in the second horizontal direction and/or in the vertical direction as a function of a critical field extent of a main magnetic field and/or of a gradient field within the patient receiving area, whereby a simple positioning of the patient can likewise be made possible. This likewise enables a simple and optimal positioning of the patient within the patient receiving area to be achieved, and thus also yields a high image quality of the subsequent image data in the subsequent magnetic resonance examination. In addition, the processing unit can also take into account a dimension of the patient receiving area, so that too small a distance between the patient (e.g., the patient's head), and a housing surrounding the patient receiving area can be prevented. Additionally or alternatively, the processing unit can also take into account a region of the patient to be examined in determining the position of the patient table in the vertical direction.

In an advantageous development of the disclosure, there can be a provision for the processing unit to determine a position of the patient table in the second horizontal direction and/or in the vertical direction as a function of information about position-dependent image artifacts. The information about position-dependent image artifacts can be stored in a database for example in such cases, and be read out by the processing unit for determining the position of the patient table and/or of the patient. In this case, the information about position-dependent image artifacts can be obtained for similar magnetic resonance examinations. Determining the position of the patient table in the second horizontal direction and/or in the vertical direction may include a position of the patient table in which undesired artifacts are suppressed in the acquired image data. For example, in such cases imaging areas that could lead to image artifacts are arranged outside the FoV and/or the critical field extent of the magnetic resonance system. In this way, undesired fault effects in the image data acquisition (e.g., image artifacts), can already be advantageously prevented.

In an advantageous development of the disclosure, there can be a provision for the position of the patient table determined by the processing unit in the second horizontal direction and/or in the vertical direction within the patient receiving area to be output to a user as a suggestion for a positioning of the patient table for the impending magnetic resonance examination. The suggestion may be output by means of an output unit of a user interface of the magnetic resonance system. The output unit can be arranged in the control room in this case, wherein the control room is embodied arranged separately from the examination room within which the scanner unit of the magnetic resonance system is arranged. Moreover the suggestion can also be output at a user interface within the examination room, such as for example at a monitor and/or a display that is arranged on the scanner unit and/or the patient support. This embodiment thus makes it possible for the user to be able to check the position of the patient table once more and/or adapt it to patient-specific characteristics. If, for example, a patient who is inclined to experience claustrophobia is positioned on the patient table, the user can reject the suggestion for positioning in the second horizontal direction and/or in the vertical direction.

In an advantageous development of the disclosure, there can be a provision for the displacement of the patient table in the second horizontal direction and/or in the vertical direction within the patient receiving area to be controlled automatically by means of the processing unit. This makes possible an especially simple and time-saving positioning of the patient table within the patient receiving area for a magnetic resonance examination.

In an advantageous development of the disclosure, there can be a provision before the acquisition of the medical magnetic resonance data for a control measurement to be carried out. A control measurement is to be understood in this context as a measurement to acquire magnetic resonance data, wherein by means of the magnetic resonance data acquired in this way, the position of the patient within the patient receiving area can be checked and/or controlled with respect to image quality and/or the region to be examined. A control measurement of this type may advantageously exhibit a lower resolution in the acquired image data. A check based on the acquired image data of the control measurement can be undertaken manually by the user in this case and/or also at least partly automatically by means of the processing unit. In this way, for example the position of the patient in the second horizontal direction and/or in the vertical direction can be checked before the medical magnetic resonance examination and, if required, a repositioning may be carried out, such as if the position in the second horizontal direction and/or in the vertical direction is unfavorable for the impending medical magnetic resonance system.

Furthermore, the disclosure is based on a magnetic resonance system with a scanner unit, which has a basic field magnet, a gradient coil unit, and a radio-frequency antenna unit, a patient receiving area surrounded by the scanner unit, and a patient support with a movable patient table able to be moved in the first horizontal direction, in the second horizontal direction, and/or in the vertical direction.

In an embodiment, the patient support has a first horizontal adjustment unit, by means of which an adjustment of a movement and/or position of the patient table in the first horizontal direction is made. Furthermore, the patient support can have a second horizontal adjustment unit, by means of which an adjustment of a movement and/or position of the patient table in the second horizontal direction is made. The second horizontal adjustment unit may be configured to adjust a movement and/or position of the patient table in the second direction within the patient receiving area. Furthermore, the patient support can have a vertical adjustment unit, by means of which an adjustment of a movement and/or position of the patient table in the vertical direction is made. The vertical adjustment unit may be configured to adjust a movement and/or position of the patient table in the vertical direction within the patient receiving area.

In an embodiment of the magnetic resonance system, as a result of a displacement and/or a positioning of the patient table in the second horizontal direction and/or in the vertical direction, imaging regions and/or materials that are not included in the region of the patient to be examined can be positioned outside a critical field extent of the magnetic field of the magnetic resonance system for the acquisition of medical magnetic resonance data. As a result hereof, fault effects in the acquired image data (e.g. image artifacts), can be reduced and/or prevented.

In an advantageous development of the magnetic resonance system embodiment, there can be a provision for the magnetic resonance system to be designed for carrying out a method for positioning a patient within a patient receiving area for a magnetic resonance examination.

In an embodiment, it can advantageously be achieved that fault effects in the image data (e.g. image artifacts), can be reduced and/or prevented. For instance, because of a displacement and/or a positioning of the patient table in the second horizontal direction and/or in the vertical direction, imaging regions and/or materials that are not included in the region of the patient to be examined can be positioned outside a critical field extent and/or outside a critical field area of the magnetic field of the magnetic resonance system for the acquisition of medical magnetic resonance data.

Moreover, as a result of the positioning of the patient in the second horizontal direction and/or in the vertical direction within the patient receiving area, an advantageous positioning of the region of the patient to be examined within the isocenter of the magnetic resonance system can be achieved, thus yielding an optimal condition for a high image quality of the acquired magnetic resonance image data to be provided.

The advantages of the magnetic resonance system embodiments described herein essentially correspond to the advantages of the method embodiments for positioning a patient within a patient receiving area for a magnetic resonance examination, which have been explained above in detail. Features, advantages, or alternate forms of embodiments mentioned throughout the disclosure can likewise be transferred to the other claimed subject matters (e.g., other embodiments), and vice versa.

In an advantageous development of the embodiments of the magnetic resonance system, there can be a provision for the patient support to have a horizontal adjustment unit and a vertical adjustment unit, by means of which the patient table is able to be moved within the patient receiving area in the second horizontal direction and/or in the vertical direction. This advantageously enables imaging areas and/or materials that are not included in the region of the patient to be examined to be positioned outside a critical field extent of the magnetic field.

In an advantageous development of the embodiments of the magnetic resonance system, there can be a provision for the magnetic resonance system to have a processing unit, which is designed to control a movement of the patient table in the second horizontal direction and/or in the vertical direction within the patient receiving area. The processing unit may be configured to perform automatic control of the first horizontal adjustment unit, the second horizontal adjustment unit, and/or the vertical adjustment unit. This enables a simple and rapid control of the first horizontal adjustment unit, the second horizontal adjustment unit, and/or the vertical adjustment unit, and thus a simple and rapid control of a movement of the patient table in the first horizontal direction, the second horizontal direction, and/or in the vertical direction to advantageously be achieved.

The disclosure is further based on a computer program product (e.g., a non-transitory computer-readable media), which comprises a program and may be loaded onto a memory of a programmable control unit, with program means for carrying out a method for positioning a patient within a patient receiving area for a magnetic resonance examination when the program is executed by the control unit. In this case, the computer program might utilize, for instance, program means, e.g. libraries and auxiliary functions, to realize the corresponding forms of embodiment of the method. In such cases, the computer program can comprise software with source code may be compiled and linked, or that only has to be interpreted, or an executable software code that only has to be loaded into a corresponding processing unit for execution.

The computer program product embodiments able to be loaded directly onto a memory of a programmable processing unit, and has program code means for carrying out an inventive method when the computer product is executed in the processing unit. The computer program product can be a computer program or one or more executable portions of a computer program. This enables the method embodiments described herein to be carried out quickly, identically repeatably, and robustly. The computer program product may be configured in such a way that it can carry out the method embodiments by means of the processing unit. The processing unit may, in this case, fulfill the corresponding requirements such as, for example, an appropriate main memory, an appropriate graphics card, or an appropriate logic unit, so that the respective method steps can be carried out.

The computer program product may be stored on a computer-readable storage medium (e.g., a non-transitory computer-readable media) for example, or stored on or otherwise accessed via a network or server, from where it can be loaded into the processor of a local processing unit, which can be embodied directly connected to it or as a part of it. Furthermore, control information of the computer program product can be stored on an electronically-readable data medium. The control information of the electronically readable data medium can be embodied in such a way that, when the data medium is used in a processing unit, it carries out the method embodiments described herein. In this way, the computer program product can also represent the electronically readable data medium. Examples of electronically readable data media include a DVD, a magnetic tape, a hard disk, or a USB stick, on which electronically readable control information (e.g., software), may be stored. When this control information (software) is read from the data medium and stored in a controller and/or processing unit, one or more (or all) of the method embodiments described herein can be carried out. In this way, the disclosure can also be based on the said computer-readable medium and/or on the said electronically readable data medium.

FIG. 1 shows an example magnetic resonance system as a schematic diagram, in accordance with an embodiment of the present disclosure. As shown in FIG. 1, a magnetic resonance system 10 is shown schematically. The magnetic resonance system 10 comprises a scanner unit 11 formed from a magnet unit, which comprises a superconducting main magnet 12 for creating a strong and constant main magnetic field 13. Moreover, the magnetic resonance system 10 has a patient receiving area 14 for receiving a patient 15. The patient receiving area 14 in the present exemplary embodiment is configured in the shape of a cylinder, and is surrounded in a circumferential direction by the scanner unit 11. This is by way of example and not limitation, and other embodiments of the patient receiving area 14 may differ from a cylindrical shape as shown in FIG. 1, and may include any suitable shape. For example, embodiments include the patient receiving area 14 being open to the side and surrounded by the scanner unit 11 in a 'C' shape.

The patient 15 can be pushed and/or moved into the patient receiving area 14 by means of a patient support 16 of the magnetic resonance system 10. To this end, the patient support 16 has a patient table 17 configured to be movable within the patient receiving area 14. The patient support 16 also has a base unit 18, which is arranged outside the patient receiving area 14. The mobile patient table 17 is arranged and/or supported on the base unit 18.

For movement of the patient table 17 and/or for positioning of the patient 15 within the patient receiving area 14, the magnetic resonance system 10 (e.g. the patient support 16), additionally has a first horizontal adjustment unit 19, a second horizontal adjustment unit 36, and a vertical adjustment unit 20. The first horizontal adjustment unit 19 in this case is included in the base unit 18. Likewise, the second horizontal adjustment unit 36 is included in the base unit 18, and the vertical adjustment unit 20 is included in the base unit 18.

By means of the first horizontal adjustment unit 19, the patient table 17 can be pushed or moved in a first horizontal direction 21. For instance, the patient table 17 can be moved by means of the first horizontal adjustment unit 19 in the first horizontal direction 21 into the patient receiving area 14. The first horizontal direction 21 may include a direction of a longitudinal extent of the patient table 17 and/or a direction of a longitudinal extent of the patient receiving area 14.

By means of the second horizontal adjustment unit 36, the patient table 17 can be pushed and/or moved in a second horizontal direction 37. For instance, the patient table 17 can be pushed and/or moved by means of the second horizontal adjustment unit 19 in the second horizontal direction 21 within the patient receiving area 14. The second horizontal direction 21 may include a direction of width of the patient table 17. Moreover, the second horizontal direction 21 is aligned at right angles to the first horizontal direction 21.

By means of the vertical adjustment unit 20, the patient table 17 can be pushed and/or moved within the patient receiving area 14 in a vertical direction 22. The vertical direction 22 may include a direction that is essentially parallel to a weight force acting on the patient table 17 or that is essentially antiparallel and/or opposed to a weight force acting on the patient table 17. Moreover, the vertical direction 22 is aligned at right angles to the first horizontal direction 21 and at right angles to the second horizontal direction 37.

In an embodiment, each of the first horizontal adjustment unit 19, the second horizontal adjustment unit 36, and the vertical adjustment unit 20 may be implemented with any suitable number and/or type of drive elements to facilitate the movement and positioning of the patient table 17 in one or more of the first horizontal direction, the second horizontal direction, and/or the vertical direction as discussed herein. These drive elements may include, for example, motors (e.g., stepper motors), belts, chains, cords, gears, etc., configured in any suitable manner to enable the movement of each of the first horizontal adjustment unit 19, the second horizontal adjustment unit 36, and the vertical adjustment unit 20.

The drive elements may be electronically controllable, and such electronic control may take place via one or more control signals generated via the processing unit 31, which may be coupled to the drive elements of one or more of the first horizontal adjustment unit 19, the second horizontal adjustment unit 36, and the vertical adjustment unit 20. Thus, the processing unit 31 may generate control signals that represent a desired direction, position, speed, etc., instructing the drive elements of one or more of the first horizontal adjustment unit 19, the second horizontal adjustment unit 36, and the vertical adjustment unit 20 to move the patient support 16 and, in turn the patient table 17 to a desired position. In some embodiments, the drive elements may include feedback (e.g., via a stepper motor or an encoder attached to the drive elements), which may facilitate the processing unit 31 ensuring that the patient support 16 and, in turn, the patient table 17 is driven to the correct position.

Again, the illustrations shown in FIG. 1 are for purposes of explanation and are by way of example and not limitation. For instance, embodiments of the patient support 16 may differ from those shown in FIG. 1. For example, the patient support 16 may be configured such that an arrangement of the vertical adjustment unit 20, the first horizontal adjustment unit 19, and/or the second horizontal adjustment unit 36 are included within or as part of the patient support 16. Moreover, an arrangement of the patient table 17 on the base unit 18 can also differ from the arrangement described above.

The scanner unit 11 (e.g., the magnet unit) may also have a gradient coil unit 23 configured to generate magnetic field gradients, which are used for spatial encoding during an imaging. The gradient coil unit 23 is controlled by means of a gradient control unit 24 of the magnetic resonance system 10. The scanner unit 11 (e.g. the magnet unit) may further include a radio-frequency antenna unit 25 for excitation of a polarization that arises in a main magnetic field 13 that is created by the main magnet 12. The radio-frequency antenna unit 25 is controlled by a radio-frequency antenna control unit 26 of the magnetic resonance system 10 and irradiates radio-frequency magnetic resonance sequences into the patient receiving area 14 of the magnetic resonance system 10.

For control of the main magnet 12, of the gradient control unit 23 and for control of the radio-frequency antenna unit 25, the magnetic resonance system 10 has a control unit 27. The control unit 27 centrally controls the magnetic resonance system 10, such as for example the carrying out of a predetermined gradient echo sequence. Moreover, the control unit 27 comprises an evaluation unit not shown in greater detail for the evaluation of medical image data, which is acquired during the magnetic resonance examination.

Furthermore, the magnetic resonance system 10 comprises a user interface 28 that is connected to the control unit 27. Control information such as, for example, imaging parameters, as well as reconstructed magnetic resonance images, can be displayed on an output unit 29, which may include for example at least one monitor of the user interface 28 that may be viewed a medical operator. Furthermore, the user interface 28 has an input unit 30, by means of which information and/or parameters can be entered by the medical operators during a measurement process.

The scanner unit 11 is arranged together with the patient support 16 within an examination room 33. The control unit 27 with the user interface 28, on the other hand, is arranged within a control room 34, which is embodied separately and decoupled from the examination room 33.

The magnetic resonance system 10 shown can of course comprise additional, less, or alternate components as understood to be part of the ordinary operation of magnetic resonance facilities. Moreover, the general manner in which a magnetic resonance system 10 works is known to the person skilled in the art, so that a more detailed description of the further components will not be provided here.

For controlling the first horizontal adjustment unit 19, the second horizontal adjustment unit 36, and the vertical adjustment unit 20, the magnetic resonance system 10 has a processing unit 31. The processing unit 31 may be implemented as any suitable number and/or type of processor circuitry, which may include pure hardware implementation of combinations of processors and other software executable code. In the present exemplary embodiment, the processing unit 31 is integrated within the control unit 27 of the magnetic resonance system 10. Additionally or alternatively, the processing unit 31 can also be embodied and/or arranged separately from the control unit 27 within the magnetic resonance system 10. For example, the processing unit 31 can also be included as part of the patient support 16.

FIG. 2 shows a flow diagram of an example method for positioning a patient within a patient receiving area for a magnetic resonance examination, in accordance with an embodiment of the present disclosure. In an embodiment, the processing unit 31, together with the patient support 16, may be configured to execute individual method steps associated with the method 200 as shown and described herein with reference to FIG. 2.

As further discussed below, the method embodiments may be performed to position the patient 15 within the patient receiving area 14 for a magnetic resonance examination. To this end, the processing unit 31 may further implement computer programs and/or software, which are designed for carrying out method 200 for positioning the patient 15 within the patient receiving area 14 for a magnetic resonance examination appropriately when the computer programs and/or software are executed by means of the processing unit 31, such as via a processing unit 31 and/or logic unit of the processing unit 31 not shown in any greater detail.

The software and/or computer programs may be stored in a memory unit not shown in any greater detail in FIG. 1. The memory unit in this case can be included in the processing unit 31. Moreover, it is also conceivable for a memory unit to be included in the control unit 27. Additionally or alternatively, the memory unit can also comprise an external memory unit. Such an external memory unit can be integrated within the magnetic resonance system 10 or implemented separately and/or externally from the magnetic resonance system 10. For example, an external memory unit can also be arranged and/or integrated as part of a cloud computing arrangement that is accessible in any suitable manner.

The method 200 may begin with an initial positioning (block 201) of the patient 15 on the movable patient table 17 of the patient support 16. This may also include positioning (block 201) of any supplementary units that might be needed on the patient 15, such as for example one or more of an electrocardiogram (EKG) unit, an infusion unit, a respiration belt, a local radio-frequency antenna unit, etc. The patient 15 may be positioned manually (block 201) in such cases by the medical operating staff.

The method 200 may include the initial positioning (block 201) including one or more provisions for the user, which may be considered by the medical operating staff and controlled by the processing unit 31 to obtain information relating to the positioning of the patient 15 on the patient table 17 and/or information relating to a positioning of a supplementary unit on the patient 15 via an output unit 32. To this end, the magnetic resonance system 10 as shown in FIG. 1 may include a further user interface 35 with the output unit 32, which is arranged within the examination room 33. The output unit 32 of the further user interface 35 in this case can be arranged directly on the scanner unit 11, in particular on a front side of the scanner unit 11, or can also be arranged on the patient support 16.

The method 200 may include moving and/or positioning (block 202) of the patient table 17 and thus of the patient 15 in the first horizontal direction 21 until a region of the patient to be examined 15 is arranged in a FoV of the patient receiving area 14. The movement and/or positioning (block 202) of the patient table 17 in the first horizontal direction 21 is performed by means of the first horizontal adjustment unit 19 of the patient support 16. The first horizontal adjustment unit 19 may be controlled in this case by means of the processing unit 31. For this purpose, the processing unit 31 may comprise software and/or computer programs, which are designed to control the first horizontal adjustment unit 19 when executed. For example, the processing unit 31 can determine a position of the patient table 17 within the patient receiving area 14 with reference to the region of the patient to be examined 15. The position determined in the horizontal direction 21 can subsequently be output to the user, in particular the medical operating staff, via the output unit 32, which may be arranged directly on the patient support 16 and/or on the scanner unit 11, so that said user only has to confirm the position in the first horizontal direction 21 and that the processing unit 31, supported by the first horizontal adjustment unit 21, executes the positioning automatically and/or autonomously.

The method 200 may also include the position of the patient 15 and thus also of the patient table 17 being predetermined (block 202) by the medical operating staff. In this case, for example the medical operating staff can enter (block 202) the position by means of the further user interface 35. Provided the medical operating staff predetermines a position of the patient 15, this can be converted into a position of the patient table 17 within the patient receiving area 14 by the processing unit 31. The position of the patient 15 and/or of the patient table 17 entered by the medical operating staff can then subsequently by adjusted by means of the first horizontal adjustment unit 19, controlled by the processing unit 31.

After the positioning of the patient table 17 in the first horizontal direction 21, the method 200 may include moving and/or positioning (block 203) of the patient table 17 in the second horizontal direction 37 and/or in the vertical direction 22 within the patient receiving area 14. The positioning and/or moving of the patient table 17 in the second horizontal direction 37 and/or in the vertical direction 22 within the patient receiving area 14 is performed by means of the second horizontal adjustment unit 36 and/or the vertical adjustment unit 20, wherein the second horizontal adjustment unit 36 and/or the vertical adjustment unit 20 is controlled by the processing unit 31.

Imaging areas and/or materials that are not included in the region of the patient to be examined 15, such as for example the arms of the patient 15 for a liver examination, can be positioned outside a critical field extent of a magnetic field of the magnetic resonance system 10 by shifting the patient table 17 in the second horizontal direction 37 and/or in the vertical direction 22 for the acquisition of medical magnetic resonance data. A field extent of the magnetic field within the patient receiving area 14 is described by an overlaying of a main magnetic field 13 with a gradient field. In edge areas of the patient receiving area 14 a field strength of the magnetic field drops away and leads to a critical field extent of the magnetic field. Objects that are arranged within the critical field extent can lead to undesired faults in the acquisition of magnetic resonance data.

The method 200 may include the processing unit 31 automatically and/or autonomously determining (block 203) a position of the patient 15 and/or of the patient table 17 in the second horizontal direction 37 and/or in the vertical direction 22 as a function of the planned magnetic resonance examination. If, for example, the magnetic resonance examination comprises a head examination on the patient 15, a vertical position of the patient table 17 can be determined (block 203) by the processing unit 31 in such a way that the head of the patient 15 has an optimal position for an acquisition of image data. For example, the processing unit 31 can define a position of the patient 15 and/or of the patient table 17 in such a way that the region of the patient 15 to be examined is positioned within an isocenter of the scanner unit 11 and possibly disruptive areas for the impending magnetic resonance examination are arranged outside the FoV and/or the critical field extent. The processing unit 31 can also take into account a dimension of the patient receiving area 14 in the determination (block 203) of the position of the patient table 17 in the vertical direction 22, so that too small a distance between the patient 15 and a housing surrounding the patient receiving area 14 can be prevented. For example, the position of the patient 15 and/or of the patient table 17 in the vertical direction 22 can be dependent on a diameter of the patient receiving area 14 of the magnetic resonance system 10.

Furthermore, for example, in this head examination on the patient 15 by the processing unit 31, a position in the second horizontal direction 37 of the patient table 17 can be determined (block 203) in such a way that the head of the patient 15 has an optimal position for an image data acquisition. The processing unit 31 can define a position of the patient 15 and/or of the patient table 17 in such a way that the region of the patient 15 to be examined is positioned within the isocenter of the scanner unit 11 and possibly disruptive areas for the impending magnetic resonance examination in the second horizontal direction 37 are arranged outside the FoV and/or the critical field extents. The processing unit 31 can also take into account a dimension of the patient receiving area 14 in the determination (block 203) of the position of the patient table 17 in the second horizontal direction 37, so that too small a distance between the patient 15 and a housing surrounding the patient receiving area 14 can be prevented. For example, the position of the patient 15 and/or of the patient table 17 in the second horizontal direction 37 can also be dependent on a diameter of the patient receiving area 14 of the magnetic resonance system 10.

Moreover in magnetic resonance examinations in which the head of the patient 15 is arranged and/or positioned within the patient receiving area 14, a position of the patient 15 and/or of the patient table 17 in the second horizontal direction 37 and/or in the vertical direction 22 can be determined (block 203) in such a way that the head of the patient 15 is arranged with a sufficiently large distance to the housing of the patient receiving area 14, in order to avoid the patient 15 experiencing states of anxiety and/or feeling unwell.

Furthermore, the processing unit 31 can determine (block 203) a position of the patient 15 and/or of the patient table 17 in the second horizontal direction 37 and/or in the vertical direction 22 automatically and/or autonomously as a function of a critical field extent of a main magnetic field 13 and/or of a gradient field within the patient receiving area 14. For example, for a liver examination of the patient 15, the patient 15 can be displaced in the second horizontal direction 37 and/or in the vertical direction 22 in such a way that the arms of the patient 15 are no longer arranged in an imaging area within the patient receiving area 14.

In this way, the processing unit 31 can also determine (block 203) the position of the patient table 17 and/or the position of the patient 15 in the second horizontal direction 37 and/or in the vertical direction 22 as a function of Information about position-dependent image artifacts. In this case, the information about position-dependent image artifacts for a specified and/or defined examination can be stored in a database by the processing unit 31, and the processing unit 31 can access the database by means of a data network not shown in FIG. 1 in greater detail. The database, in this case, can be integrated within the magnetic resonance system 10 or can also comprise an external database. The information about the position-dependent image artifacts can also stem from previously conducted, similar magnetic resonance examinations. For example, the position of the patient table 17 and/or of the patient 15 in the second horizontal direction 37 and/or in the vertical direction 22 can be determined (block 203) by means of the processing unit 31 in such a way that undesired artifacts in the acquired image data are suppressed and/or eliminated. In such cases, imaging materials, for example imaging areas that are arranged next to the region of the patient to be examined 15, are arranged outside the FoV and/or the critical field extent within the patient receiving area 14.

The position of the patient 15 and/or of the patient table 17 in the second horizontal direction 37 and/or in the vertical direction 22 within the patient receiving area 14 determined (block 203) by the processing unit 31 can be output to the user as a suggestion for a positioning of the patient 15 and/or of the patient table 17 for the impending magnetic resonance examination, such as to the medical operating staff. The suggestion may be output by means of the output unit 32, which can be arranged directly on the scanner unit 11 and/or the patient support 16. The user thus has the option of checking the positioning suggestion and, if necessary, correcting the suggested position. When the user enables the position in the second horizontal direction 37 and/or in the vertical direction 22, then performance of an automatic and/or autonomous positioning of the patient 15 and/or of the patient table 17 in the second horizontal direction 37 and/or in the vertical direction 22 by means of the vertical adjustment unit 20 and/or the second horizontal adjustment unit 36 may take place, which may be controlled by the processing unit 31.

Alternatively, there can be provision for the position of the patient 15 and/or of the patient table 17 in the second horizontal direction 37 and/or in the vertical direction 22 determined (block 203) by the processing unit 31 to be set directly by the processing unit 31 together with the vertical adjustment unit 20 and/or the second horizontal adjustment unit 36 automatically and/or autonomously.

The method 200 may include the position of the patient 15 and/or of the patient table 17 being determined (block 203) by the processing unit 31 and then being converted to control signals, which lead in the vertical adjustment unit 20 and/or the second horizontal adjustment unit 36 to a movement of the patient table 17 into the position determined. The position of the patient 15 and/or of the patient table 17 thus determined may be converted into control signals in such case by means of the corresponding software and/or the corresponding computer programs of the processing unit 31.

Moreover, there can be provision for checking the positioning process of the patient 15 and/or of the patient table 17, for a control measurement to be carried out, so that there can be a check made on the positioning of the patient 15 by the user.

The method 200 may include acquiring (block 204) medical magnetic resonance data of the region of the patient to be examined 15 by means of the scanner unit 11. The method 200 may include, for the acquisition of magnetic resonance data in this manner, the patient table 17, and thus the patient 15, being located in an optimal position (e.g., a position known to produce the least image artifacts or otherwise known to produce the best results) in the first horizontal direction 21, the second horizontal direction 36, and in the vertical direction 22.

Although the embodiments of the disclosure have been illustrated and described in detail using the preferred exemplary embodiment, the disclosure is not limited by the disclosed examples, and a person skilled in the art can derive other variations therefrom without departing from the scope of protection of the disclosure.

What is claimed is:

1. A method for positioning a patient within a patient receiving area of a magnetic resonance scanner to perform a magnetic resonance examination, the method comprising:

positioning the patient on a movable patient table of a patient support;

controlling, via processor circuitry, one or more drive elements associated with the patient table to move the patient table in a first horizontal direction until a first region of the patient to be examined is arranged in a Field of View (FoV) of the magnetic resonance system, controlling, via the processor circuitry, the one or more drive elements associated with the patient table to move the patient table in a second horizontal direction and/or to move the patient table in a vertical direction within the patient receiving area to position the first region of the patient within a detection area of the magnetic resonance system within which magnetic resonance signals are acquired, and to position a second region of the patient outside the detection area and outside a critical field extent of a magnetic field of the magnetic resonance system; and acquiring, via the magnetic resonance scanner, medical magnetic resonance data of the first region of the patient to be examined, wherein the positioning of the first region of the patient and the second region of the patient prevents objects within the second region of the patient from causing artifacts in the medical magnetic resonance data that is acquired with respect to the first region of the patient.

2. The method as claimed in claim 1, wherein the processor circuitry is configured to determine a position of the patient table in the second horizontal direction and/or in the vertical direction as a function of information included as part of a planned magnetic resonance examination.

3. The method as claimed in claim 1, wherein the processor circuitry is configured to determine a position of the patient table in the second horizontal direction and/or in the vertical direction as a function of a critical field extent of a main magnetic field and/or of a gradient field within the patient receiving area.

4. The method as claimed in claim 1, wherein the processor circuitry is configured to determine a position of the patient table in the second horizontal direction and/or in the vertical direction as a function of information about position-dependent image artifacts.

5. The method as claimed in claim 1, wherein the processor circuitry is configured to output the determined position of the patient table in the second horizontal direction and/or in the vertical direction within the patient receiving area to a display that is arranged on the magnetic resonance scanner and/or the patient support as a suggestion for a positioning of the patient table for the magnetic resonance examination.

6. The method as claimed in claim 1, further comprising:
automatically controlling, via the processor circuitry, a displacement of the patient table in the second horizontal direction and/or in the vertical direction within the patient receiving area.

7. The method as claimed in claim 1, further comprising:
executing, via the via the processor circuitry, a control measurement before the acquisition of the medical magnetic resonance data.

8. The method of claim 1, wherein the first region of the patient contains the patient's liver for which the medical magnetic resonance data is to be acquired, and wherein the second region of the patient contains the patient's arms.

9. The method of claim 1, wherein the act of controlling the one or more drive elements associated with the patient table to move the patient table in the second horizontal direction and/or to move the patient table in the vertical direction within the patient receiving area comprises positioning the patient table such that a minimum threshold distance is maintained between the patient and a housing surrounding the patient receiving area.

10. A magnetic resonance system, comprising:
a magnetic resonance scanner including a basic field magnet, a gradient coil unit, and a radio-frequency antenna unit;
a patient receiving area surrounded by the magnetic resonance scanner; and
a patient support having with a patient table that is movable with respect to the patient receiving area in each of (i) a first horizontal direction, (ii) a second horizontal direction, and (iii) a vertical direction to position a first region of a patient within a detection area of the magnetic resonance system within which magnetic resonance signals are acquired, and to position a second region of the patient outside the detection area and outside a critical field extent of a magnetic field of the magnetic resonance system,
wherein the positioning of the first region of the patient and the second region of the patient prevents objects within the second region of the patient from causing artifacts in the medical magnetic resonance data that is acquired with respect to the first region of the patient.

11. The magnetic resonance system as claimed in claim 10, further comprising:
processor circuitry configured to:
control one or more drive elements associated with the patient table to move the patient table in the first horizontal direction until the first region of the patient to be examined is arranged in a Field of View (FoV) of the patient receiving area of the magnetic resonance system, and
control one or more drive elements associated with the patient table configured to move the patient table in the second horizontal direction and/or to move the patient table in the vertical direction within the patient receiving area.

12. The magnetic resonance system as claimed in claim 10, wherein the magnetic resonance scanner is configured to acquire medical magnetic resonance data of the first region of the patient to be examined.

13. The magnetic resonance system as claimed in claim 10, wherein the patient support includes a horizontal adjustment unit and a vertical adjustment unit that are associated with the one or more drive elements, and
wherein the processor circuitry is configured to control the horizontal adjustment unit and the vertical adjustment unit via the one or more drive elements to move the patient table within the patient receiving area in the second horizontal direction and/or in the vertical direction, respectively.

14. A non-transitory computer readable media associated with a magnetic resonance system that includes a magnetic resonance scanner, the non-transitory computer readable media having instructions stored thereon that, when executed by processor circuitry, cause the magnetic resonance system to:
generate control signals to control one or more drive elements associated with a patient table of a patient support associated with the magnetic resonance system to move the patient table in a first horizontal direction until a first region of a patient to be examined is arranged in a Field of View (FoV) of a patient receiving area of the magnetic resonance system,
generate control signals to control one or more drive elements associated with the patient table to move the patient table in a second horizontal direction and/or to move the patient table in a vertical direction within the patient receiving area to position the first region of the patient within a detection area of the magnetic resonance system within which magnetic resonance signals are acquired, and to position a second region of the patient outside the detection area and outside a critical field extent of a magnetic field of the magnetic resonance system; and acquire, via the magnetic resonance scanner, medical magnetic resonance data of the first region of the patient to be examined,
wherein the positioning of the first region of the patient and the second region of the patient prevents objects within the second region of the patient from causing artifacts in the medical magnetic resonance data that is acquired with respect to the first region of the patient.

* * * * *